United States Patent [19]

Humphrey

[11] Patent Number: 4,607,922
[45] Date of Patent: Aug. 26, 1986

[54] METHOD FOR ALIGNING AN EYE EXAMINATION INSTRUMENT WITH THE EYE UNDER EXAMINATION

[75] Inventor: William E. Humphrey, San Leandro, Calif.

[73] Assignee: Humphrey Instruments Incorporated, San Leandro, Calif.

[21] Appl. No.: 598,143

[22] Filed: Apr. 9, 1984

[51] Int. Cl.$^4$ .......................... G03B 29/00; A61B 3/14
[52] U.S. Cl. ...................................... 351/208; 354/62
[58] Field of Search .......................... 351/208; 354/62

[56] References Cited
U.S. PATENT DOCUMENTS 4,252,420  2/1981  Kohayakawa ..................... 351/208
4,468,104  8/1984  Nunokawa ......................... 351/208

Primary Examiner—Rodney B. Bovernick
Attorney, Agent, or Firm—Townsend and Townsend

[57] ABSTRACT

A method for use with an eye examination instrument for automatically aligning the eye under examination with the instrument optical axis. An operator initially aligns the instrument optical axis manually with the eye under examination. A first adjustment to the initial alignment is then automatically made in the optical train of the instrument so as to laterally align the eye under examination. The size of the lateral adjustment is determined, and an axial adjustment of the optical train is automatically effected by an amount controlled by the size of the lateral adjustment so as to axially align the eye under examination, whereby the requisite axial adjustment is determined directly from the accomplished lateral adjustment without the need for intervention of the operator.

1 Claim, 3 Drawing Figures

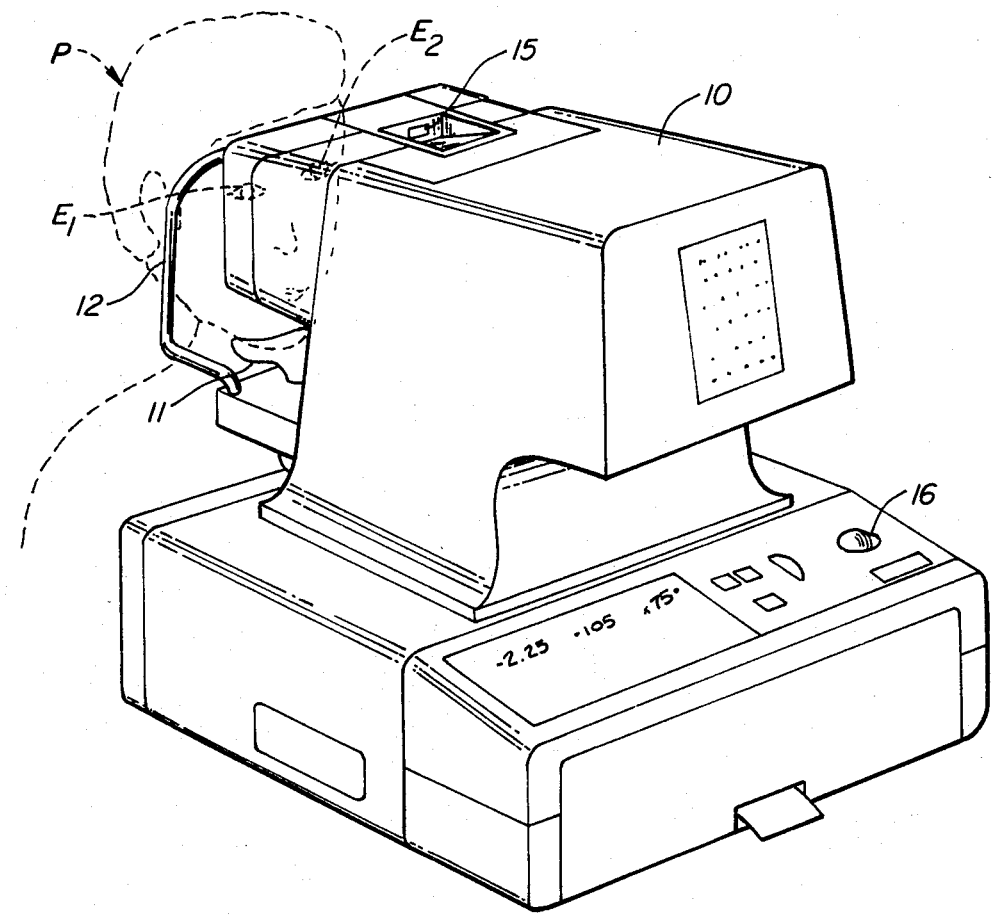
FIG._1.

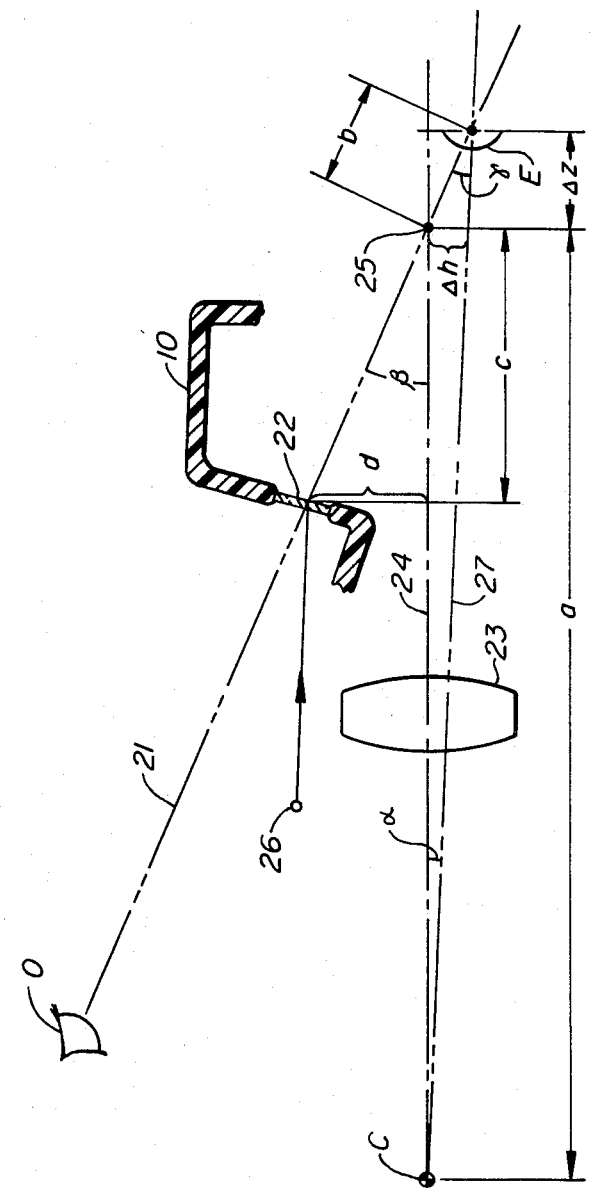
FIG._2.

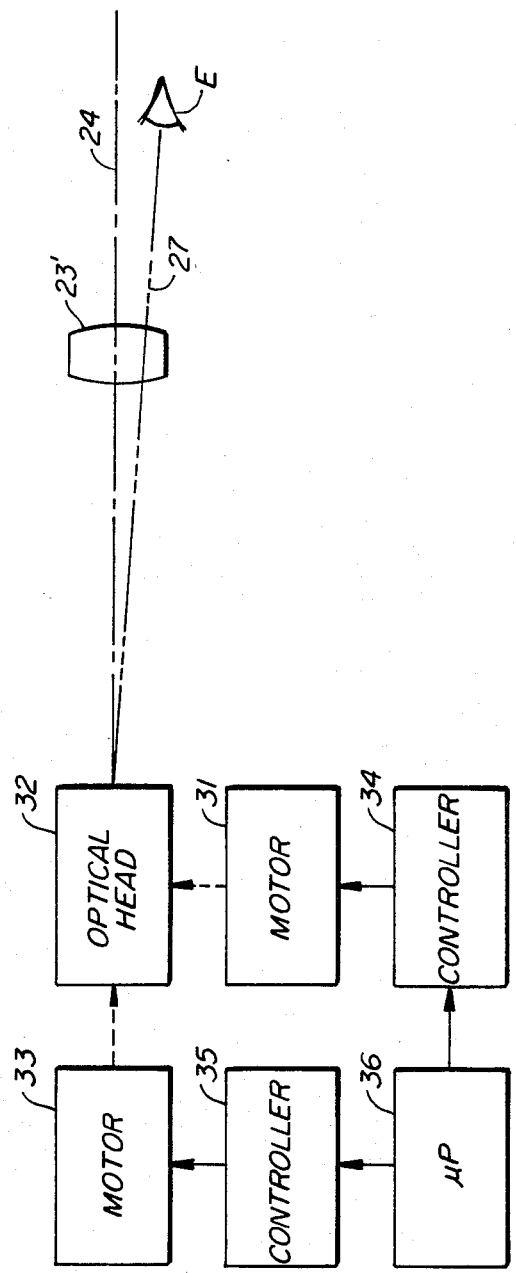
FIG._3.

METHOD FOR ALIGNING AN EYE EXAMINATION INSTRUMENT WITH THE EYE UNDER EXAMINATION

BACKGROUND OF THE INVENTION

The invention relates to the optometric examination of the human eye; more particularly, it relates to a method for automatically bringing the eye under examination and the eye examination apparatus into alignment with one another during the examination.

Apparatus such as objective refractors are commonly used to determine visual disorders of the eye and to prescribe corrective lenses. In using a typical objective refractor the patient sits before the apparatus and peers at a target, usually with his or her head held in approximately fixed position by a chin rest or other positioning member. For accurate diagnosis of refractive errors of the eye and for accurate prescription of corrective lenses, it is necessary that the eye be positioned in precise alignment with respect to the optical system of the objective refractor, and this position of alignment must be maintained while the diagnosis is being made.

A common problem faced by objective refractors is the initial acquisition of the eye under examination by the instrument's optical system and the maintenance of alignment while the visual disorders of the eye are measured. In many of the known objective refractors the instrument must be manually aligned with the eye under examination. Manual adjustment by an operator is at best of limited accuracy. For an operator who performs many examinations per day the need to manually align the instrument and eye, and to maintain that alignment during measurement, is inconvenient and annoying, with the result that the alignment is sometimes not properly carried out.

An objective refractor providing for some measure of automatic alignment of the eye is available from Humphrey Instruments, Inc. of San Leandro, Calif., and is disclosed in U.S. patent application Ser. No. 406,607, filed Aug. 9, 1982, and entitled "Objective Refractor for the Eye." The Humphrey instrument includes a projection system which casts a light pattern onto the retina of the eye under examination and which automatically analyzes the light returned from the retina. To use the Humphrey instrument, an operator first makes an initial manual adjustment of the alignment to bring the eye within the acquisition range, i.e., within the range of automatic machine alignment. The instrument includes a highly complex optical detector head which senses refractive errors in the light returned from the retina. The head is sufficiently sensitive to certain changes in the returned light pattern characteristic of lateral misalignment of the eye that it can provide a servo signal for automatic correction of the lateral misalignment. Axial misalignment can also be made to produce characteristic changes in the returned light pattern, but these were heretofore believed to be difficult to detect, difficult to correct reliably by automatic means, or at the least require sufficiently complex instrumentation that completely automatic alignment of the eye was deemed to be beyond the realm of commercial feasibility. Even though the instrument of application Ser. No. 406,607 is able to provide accurate and automatic correction of lateral misalignments, and is even able to sense to some extent the presence of axial misalignments, the designers of that commercially successful instrument still believed the intervention of a human operator was necessary to correct the axial misalignment manually as a separate operation.

SUMMARY OF THE INVENTION

The present invention provides a method of aligning the eye under examination which completely eliminates the need to rely on the eye of a human operator once an initial alignment has been achieved. A typical eye examination instrument will include an optical train for examining the eye. According to the invention an operator initially aligns the instrument optical axis manually with the eye under examination. The term "initial alignment" is used herein to refer to the alignment step performed visually by the operator. A first adjustment to the initial alignment is then automatically made in the optical train so as to laterally align the eye under examination. The size of the lateral adjustment is determined, and a second, axial adjustment of the optical train is automatically effected by an amount controlled by the size of the lateral adjustment so as to axially align the eye under examination. A feature of this aspect of the invention is that the requisite axial adjustment is determined directly from the accomplished lateral adjustment without the need for separate prior measurement of axial misalignment.

It is an object of the invention to achieve fully automated alignment of the eye with a minimum of reliance on the judgment and manual dexterity of a human operator.

It is an advantage of the invention that fully automated alignment of the eye may be achieved with the detection of only lateral misalignments of the eye. The invention completely eliminates the need for independent detection or measurement of any axial misalignment or mispositioning of the eye.

It is a further object and advantage of the invention to eliminate various common sources of inaccuracy in the determination of the refractive error of the eye. Among the sources of inaccuracy eliminated are operator error in the alignment of the instrument with the eye and vertex error and corresponding degradation of the instrument performance when the pupil of the eye does not lie in the desired plane.

Automated alignment of the eye according to the present invention also compensates for the apparent movement of the instrument optical axis if the eye should be moved.

Other objects, features and advantages of the invention will be appreciated by reference to the remaining portion of the specification and the attached drawings.

BRIEF DESCRIPTION OF THE DRAWINGS

FIG. 1 is a rear perspective view of an eye examination instrument for practicing the invention, in which a patient (shown in phantom) is positioned before the instrument;

FIG. 2 is a fragmentary view of a portion of an eye examination instrument schematically illustrating an eye under examination in a position of initial alignment with the instrument;

FIG. 3 is a schematic block diagram showing a motor control arrangement for practicing the invention.

DETAILED DESCRIPTION OF A PREFERRED EMBODIMENT

FIG. 1 shows a patient P positioned in front of the housing 10 of an objective refractor type of eye-examination instrument in preparation for an eye examination. The rear perspective view of FIG. 1 is roughly that seen by an operator of the instrument in administering the eye examination. In a typical examination the patient seats his or her chin on chin rest 11 and leans against forehead rest 12. The chin rest and forehead rest assemblies 11 and 12 serve both to maintain the patient's head in a relatively fixed position during the examination and also to establish a standard eye position for proper alignment of the optical system within the instrument housing 10.

The housing 10 includes a sight means 15 by which the operator may view the patient's eye $E_1$ or $E_2$ along a defined line of sight. The instrument also includes manual control means 16 for manually adjusting the positioning of the instruments' optical system.

To initially align the instrument with the eye under examination, the operator sights through the sight means 15 in the direction of the patient's eye. Through manual operation of the control means 16 the operator then positions the line of sight defined by sight means 15 with the pupil of the patient's eye. The manual adjustment, however, produces only an initial alignment between the eye and the instrument's optical system.

The initial positioning of the optical system with respect to the eye under examination just described and the method by which the present invention automatically brings the eye into an exact position of alignment may be understood by reference to FIG. 2. The eye under examination is denominated E, and the eye of the operator is denominated O. The sight means is provided by an inspection window 22. The operator sights along line of sight 21 through inspection window 22 into the pupil of the eye under examination E. A portion of the instrument housing 10 is also visible in FIG. 2 around inspection window 22. Within the housing 10 is an optical train, represented schematically in FIG. 2 by lens 23. In a typical objective refractor the optical train will also include an optical head for projecting an image to be viewed by the eye under examination and a detector head which may coincide with the optical head, for receiving the image from the eye and measuring the changes in the returning light rays characteristic of the refractive error of the eye. In FIG. 2 the eye under examination sights along a path passing through the point denominated C. The particular optical train utilized by the eye-examination instrument for determining the eye's refractive error is not a part of the present invention and will not be described further. For a detailed description of an optical train in connection with which the present invention may be advantageously used, reference is made to U.S. patent application Ser. No. 406,607 entitled "Objective Refractor for the Eye".

The optical axis of the optical train is designated 24. For an accurate determination of the eye's refractive error, and for an accurate prescription of corrective lenses, the eye under examination must be positioned on the optical axis at a precise predetermined distance from the reference point C. In the instrument illustrated in FIG. 2, this position is defined by the intersection of optical axis 24 with the operator's line of sight 21. The intersection point is denominated 25. To assist in initially lining up the eye under examination, the instrument illustrated in FIG. 2 includes light-emitting diode (LED) 26, which is mounted in fixed position with respect to the optical train. Inspection window 22 is provided by a partially reflecting mirror, which is inclined so as to reflect an image of LED 26 into the operator's eye O. LED 26 and the angle of partially reflecting mirror 22 are disposed so that a virtual image of LED 26 appears to the operator to lie at the intersection point 25. Thus, to bring the eye E and the optical train into initial alignment with one another, the operator merely sights along the line of sight 21 and adjusts the position of the optical train until the virtual image of LED 26 appears to coincide with the pupil of the eye under examination. Inspection window 22 may contain such means as cross hairs or the equivalent to define the line of sight precisely. The eye E in FIG. 2 is in such a position of initial alignment. It will be noted that the virtual image at intersection point 25 will appear to the operator coincident with the pupil of eye E. In actual fact, however, the eye E is slightly offset from the optical axis 24 and is displaced from the reference point C by a distance greater than the desired distance for accurate measurement of the eye.

For measurement the eye-examining instrument must "realign" the eye E. That is to say, the optical train must be adjusted such that the intersection point 25 will coincide with the pupil of eye E. As seen in FIG. 2, this adjustment will generally require two separate elemental adjustments. The first is an adjustment in a direction perpendicular to optical axis 24, which shall be referred to herein as a lateral adjustment. Although a lateral adjustment may occur in any direction perpendicular to the axis 24, of particular relevance to the present invention, for reasons explained below, is the component of the lateral adjustment lying in the plane defined by the sighting optics and the instrument optical path as illustrated in FIG. 2. The lateral adjustment is typically effected by means of a lateral or angular displacement of the optical train itself or of some portion of the optical train. The second adjustment is in the direction parallel to optical axis 24, and is referred to herein as an axial adjustment.

As has been discussed above, detector heads are known which can automatically acquire and align the eye in the lateral direction. Such a detector head is disclosed in the above-referenced U.S. patent application Ser. No. 406,607. However, it has always been deemed necessary in the past to interpose the judgment of the operator so as to align the eye in the axial direction. A reason for this has been either the difficulty in accurately aligning the eye in the axial direction by automatic means or the perceived instrumental complexity to achieve that result.

The present invention takes advantage of the ability of a detector head to accurately align the eye in the lateral direction for the purpose of accurately aligning the eye in the axial direction. In the example of initial alignment shown in FIG. 2, the eye under examination is positioned slightly below optical axis 24 and slightly too far from the reference point C. The distances and angles indicated in FIG. 2 may be described as follows: The quantity a is the separation of the desired measurement point 25 from the reference point C; the quantity b is the separation of the pupil of eye E from the measurement point 25 measured along the line of sight 21 of eye O; the quantity c is the separation in the direction parallel to optical axis 24 of measurement point 25 (and also of the virtual image of LED 26) from the point of refraction through mirror 22; the quantity d is the vertical distance of that point of refraction from optical axis 24; the quantity $\Delta z$ is the horizontal distance in a direction parallel to optical axis 24 of the pupil of eye E from measurement point 25; the angle $\alpha$ is the angle at reference point C between optical axis 24 and the line 27 to eye E; the angle $\beta$ is the angle at measurement point 25 between optical axis 24 and the line of sight 21 of the eye O; and the angle $\gamma$ is the angle at the pupil of the eye E between line of sight 21 and line 27.

In the configuration of FIG. 2 lateral alignment of eye E causes the eye to move vertically through a distance $\Delta h$ to optical axis 24. Axial alignment of the eye E requires that the distance of the eye from reference point C be reduced by the quantity $\Delta z$.

The present invention calls for automatically effecting a first adjustment of the optical train so as to laterally align the eye E, much as is done in the prior art, except for the important distinction that now a measurement is made of the amount of adjustment the optical train undergoes in the process of lateral alignment.

The vertical component of that adjustment is then used as the basis for performing a second adjustment in the axial direction leading to axial alignment of the eye. By "vertical component" is meant that component of the lateral adjustment lying in the plane of the sighting optics and the instrument optical axis. The axial adjustment calls for reducing the distance between the pupil of eye E and the reference point C by the amount $\Delta z$. While the amount of the reduction $\Delta z$ may be expressed mathematically in terms of a number of different parameters, some of the possible mathematical formulations may be difficult or expensive, if not impossible, to implement in practice. According to the present invention it has been found particularly useful for implementation of the instrumentation to express the amount of reduction $\Delta z$ in terms of the unknown angle $\alpha$ about reference point C. The reason is that in the specific embodiment illustrated herein the vertical transverse alignment is accomplished by rotation about an axis, which can conveniently be taken as passing through reference point C. Many difficulties of the instrumentation may be avoided when $\alpha$ is taken as the independent variable and as the measure of the vertical adjustment $\Delta h$ necessary for lateral acquisition. The axial adjustment $\Delta z$ may be related to the angle $\alpha$ as follows:

$$\Delta z = \frac{a \sin\alpha}{\tan\gamma} = \frac{a \sin\alpha}{\tan(\beta - \alpha)} \quad [\text{Eq. 1}]$$

In Equation 1 the quantities a and $\beta$ are fixed by the construction and arrangement of the eye examination instrument itself. The quantity $\alpha$ is measured in each application of the instrument.

In a typical instrument the quantities $\alpha$ and $\Delta z$ will be small in comparison with $\beta$ and a, respectively. In this case, $\Delta z$ will be approximately equal to the quantity $\Delta h$ cot $\gamma$. The quantity cot $\gamma$ may also be approximated by the quantity cot $\beta$ + tan $\alpha$ so that to lowest order of approximation:

$$\Delta z = \Delta h \cot \beta \quad [\text{Eq. 2}]$$

Equation 2 may be used to relate the size of the axial adjustment to the size of the lateral adjustment, and in particular to the size of the vertical component of the lateral adjustment, in those instruments in which the quantities $\alpha$ and $\Delta z$ are sufficiently small.

A convenient and especially economical way of measuring the angle $\alpha$ and effecting the adjustments required for lateral and axial alignment of the eye will now be described with reference to FIG. 3. A first stepper motor 31 is coupled to the optical train, represented schematically by lens 23', so as to produce the requisite amount of vertical adjustment at the intersection point 25. Motor 31 may be conveniently coupled to the optical head 32 so as to provide a rotary movement for purposes of effecting the "lateral" alignment.

A second stepper motor 33 is coupled to optical head 32 so as to produce the necessary axial adjustment in the pathway of the optical train. Stepper motors and appropriate gear mechanisms are well known to those skilled in the art for this purpose.

A stepper motor has the advantage that it may be caused to rotate through a prescribed and controllable number of steps, each of which produces a fixed angular displacement. The use of stepper motors has been found to provide an accurate and economical way of avoiding the heretofore perceived instrumental complexities. Stepper motors 31 and 33 are controlled by motor control means 34 and 35, respectively. The preferred embodiment illustrated herein includes microprocessor 36 for providing control commands for motor control means 34 and 35.

Instead of making a direct measurement of the vertical adjustment $\Delta h$ experienced by the optical train as measured at 25, the present invention merely keeps track of the number of steps undertaken by the motor 31. In the illustrated embodiment this is achieved by a software timing loop in microprocessor 36. Those skilled in the art will appreciate that the motor control means could also be configured with counter/timer hardware components for this purpose. The technique of keeping track of the steps through which stepper motor 31 has rotated provides a simple and accurate means of making what otherwise could be a complicated measurement. Each step of the motor 31 produces a predetermined angular displacement. This, in turn, produces a predetermined change in the angle $\alpha$, the precise change in $\alpha$ depending also upon the particular gear mechansim coupling stepper motor 31 to the optical optical head 32. Typically one step of stepper motor 31 will produce a 0.0105° change in the angle $\alpha$. Thus, the angle $\alpha$ through which the optical train moves with respect to the eye E may readily be determined from the number of steps of motor 31. From the computed value of $\alpha$, the corresponding axial adjustment $\Delta z$ may be computed from Equation 1. Analogous to motor 31, a single step of motor 33 produces a predetermined axial displacement of optical head 33. For example, a single step of motor 33 may typically produce an axial adjustment of 0.002 inch. Thus, the requisite adjustment $\Delta z$ corresponds to an ascertainable number of steps of motor 33. Microprocessor 36 computes the requisite number of steps of motor 33 corresponding to those of motor 31 and communicates corresponding commands to the motor control means to effect the lateral and axial alignment.

Thus, by making the acquisition process a two step process, and through the simple expedient of keeping track of and correlating the appropriate number of steps of two stepper motors, the present invention completely, economically, and reliably automates the process by which an eye examination instrument can be made to align the eye under examination.

While the above provides a full and complete disclosure of the preferred embodiments of the present invention, various modifications, alternate constructions, and equivalents may be employed without departing from the true spirit and scope of the invention. For example, the particular eye examination instrument illustrated in FIG. 1 and described herein is offered only by way of example; the method according to the invention may be practiced with other eye examination instruments including other types of sight means for assisting the operator in making the initial alignment, such as a video camera or other electronic imaging devices. The sighting system could also include a projected reference pattern on the eye in place of the viewing system 21, 22 and 26 specifically illustrated herein. Where the invention calls for the aid of a sight means in making the initial alignment, it is understood that the term "sight means" embraces all such viewing or sighting systems. As another alternative to the illustrated embodiment, the lateral adjustment called for by the invention could be produced in a manner other than by a rotation about reference point C. Therefore, the above description and illustrations should not be construed as limiting the scope of the invention, which is defined by the appended claims.

What is claimed is:

1. A method of aligning an eye with an eye examination instrument, said instrument including an optical train for examining an eye, said optical train defining an instrument optical axis, a photosensor for indicating a lateral alignment of said eye with respect to said instrument optical axis, a first motor coupled to said optical train for effecting lateral movement with respect to a plane, said first motor responsive to output of said photosensor to effect lateral alignment of said eye with respect to said instrument optical axis, a second motor coupled to said optical train for effecting change of the optical path length thereof, and sight means for use by an operator for determining when the eye under examination is initially aligned with said instrument optical axis, said sight means intersecting said instrument optical axis within said plane so as to be common to both the line of sight of said sight means and the instrument optical axis, said method comprising the steps of:

sighting through said sight means at the eye under examination and bringing said line of sight into a position of initial lateral alignment with said eye;

activating said first motor so as to laterally align said eye with said instrument optical axis whereby said instrument undergoes a vertical displacement $\Delta h$ at said eye; and activating said second motor so as to effect a change in said optical path length by an amount $\Delta z$, where the amount $\Delta z$ is substantially equal to $\Delta h \cot \beta$, in which $\beta$ is the angle between the line of sight of said operator through said sight means and said instrument optical axis, whereby said eye is initially axially aligned by said instrument.

* * * * *